(12) United States Patent
Peters et al.

(10) Patent No.: US 7,068,048 B2
(45) Date of Patent: Jun. 27, 2006

(54) MICROWAVE SENSOR FOR MEASURING A DIELECTRIC PROPERTY OF A PRODUCT

(75) Inventors: Steffen Peters, Linnich (DE); Reinhard Knöchel, Elmshorn (DE); Wolfgang Taute, Laboe (DE); Claas Döscher, Hamburg (DE)

(73) Assignee: Trützschler GmbH & Co. KG, Mönchengladbach (DE)

( * ) Notice: Subject to any disclaimer, the term of this patent is extended or adjusted under 35 U.S.C. 154(b) by 0 days.

(21) Appl. No.: 11/056,176

(22) Filed: Feb. 14, 2005

(65) Prior Publication Data
US 2005/0179443 A1    Aug. 18, 2005

(30) Foreign Application Priority Data
Feb. 12, 2004 (EP) ................... 04003110
Mar. 5, 2004 (DE) .............. 10 2004 011 341

(51) Int. Cl.
*G01R 27/04* (2006.01)
(52) U.S. Cl. ..................... 324/636; 324/71.1
(58) Field of Classification Search ............. None
See application file for complete search history.

(56) References Cited

U.S. PATENT DOCUMENTS

| | | |
|---|---|---|
| 3,577,071 A | 5/1971 | Collins |
| 3,967,994 A | 7/1976 | Langberg |
| 4,885,527 A | 12/1989 | Lacombe et al. |
| 4,943,778 A | 7/1990 | Osaki |
| 5,455,516 A * | 10/1995 | Jean et al. ............ 324/639 |
| 5,826,458 A * | 10/1998 | Little ............... 73/73 |
| 6,411,103 B1 * | 6/2002 | Tobias et al. ........ 324/632 |
| 2003/0150266 A1 | 8/2003 | Dammig et al. |

FOREIGN PATENT DOCUMENTS

| | | |
|---|---|---|
| DE | 262 914 A1 | 12/1988 |
| DE | 102 04 328 A1 | 6/2003 |
| EP | 0 509 187 A1 | 10/1992 |
| EP | 0 889 321 A1 | 1/1999 |
| EP | 1114299 A | 3/2000 |
| FR | 2 707 396 | 1/1995 |
| GB | 1 470 592 A | 4/1977 |
| GB | 1 570 554 A | 7/1980 |
| GB | 2 400 443 A | 10/2004 |
| JP | 63-169543 | 7/1988 |
| JP | 07260462 A | 10/1995 |
| JP | 10-185839 | 7/1998 |
| JP | 11287772 A | 10/1999 |
| WO | WO 00/55606 A2 | 9/2000 |

* cited by examiner

*Primary Examiner*—Vincent Q. Nguyen
(74) *Attorney, Agent, or Firm*—Venable LLP; Robert Kinberg; Steven J. Schwarz

(57) ABSTRACT

The application relates to a microwave sensor for measuring a dielectric property, especially the density and/or moisture content of a product, having a microwave resonator, wherein a product introduced into the resonator interacts with a resonant microwave field generated in the resonator in order to determine suitable measured quantities, and is characterized in that at least two half-waves of the electric field are formed in the resonator in one direction, the product feed being effected in at least one region of high field intensity of one of the half-waves of the electric field.

34 Claims, 9 Drawing Sheets

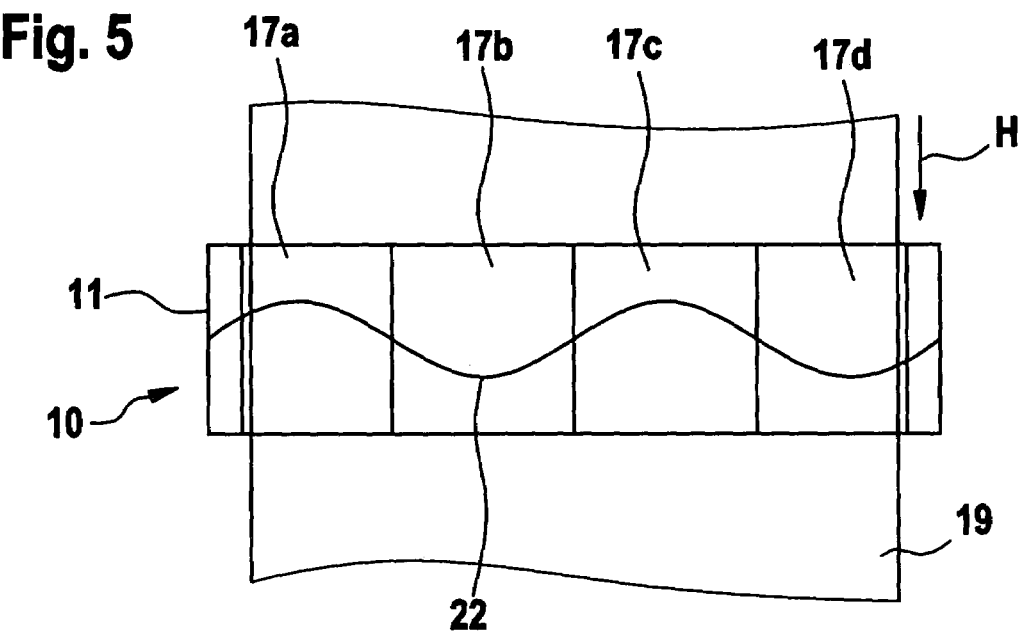
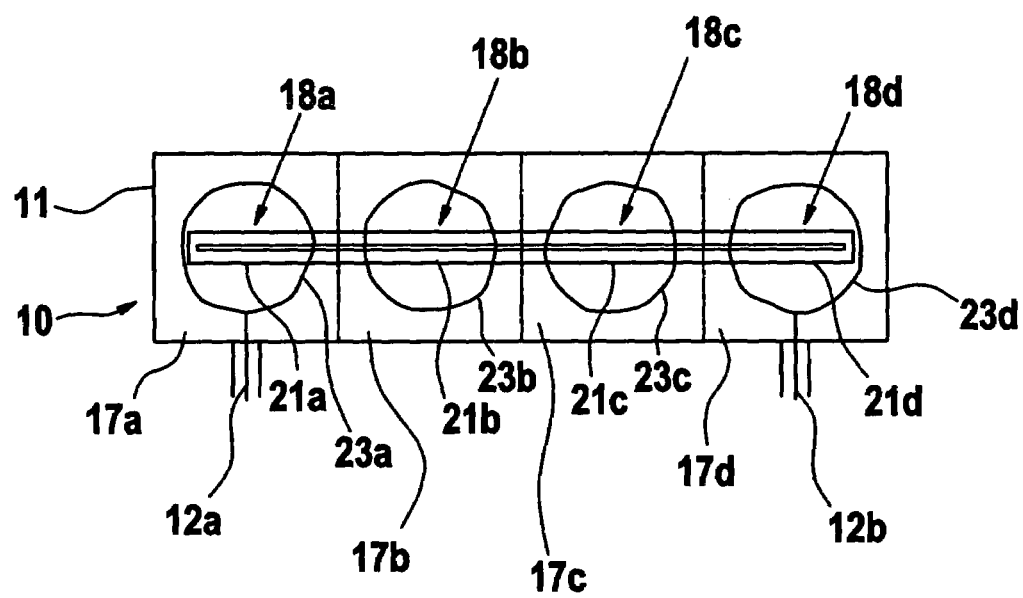

US 7,068,048 B2

MICROWAVE SENSOR FOR MEASURING A DIELECTRIC PROPERTY OF A PRODUCT

CROSS REFERENCE TO RELATED APPLICATION

This application claims priority from European Patent Application No. 04 003 110.6 dated Feb. 12, 2004 and from German Patent Application No. 10 2004 011 341.6 dated Mar. 5, 2004, the disclosure of each of which is incorporated herein by reference.

BACKGROUND OF THE INVENTION

The invention relates to a microwave sensor for measuring a dielectric property, having a microwave resonator, wherein a product introduced into the resonator interacts with a resonant microwave field generated in the resonator in order to determine suitable measured quantities related to, for example, density and/or moisture content of a product. The invention further relates to use of the sensors in a spinning preparation machine.

With such sensors, the field energy is concentrated in a specific region of the resonator. The mass loading of the resonator in the region of high field energy is limited, since too great a mass loading leads to falsification of the measuring signal owing to losses. The use of several resonators, each one only for a portion of the product, is expensive and can lead to systematic errors owing to differences in the resonators and in the corresponding control and evaluating electronics. In the case of extended, especially web-form, products, a further problem comprises the sensing of the product over a relatively large dimension, for example, across the entire width of a product web. The enlargement of the region of high field energy, for example, by enlarging the wavelength, would lead to constructions of impractical dimensions. The use of several relatively small resonators across the expanse of the product is likewise disadvantageous for the above-mentioned reasons.

EP 0 889 321 A discloses a microwave sensor for measurement on an elongate sample, having a flat, dielectric-filled resonator that has a through-bore running through it for the sample. In the measuring region arranged centrally in the resonator there is an approximately homogeneous microwave field of relatively low intensity.

DE 102 04 328 A discloses a microwave sensor for determining the mass of a fibre sliver in a spinning preparation machine, the sensor comprising a resonator having two sample volumes for two fibre slivers.

WO 00/55606 A discloses a microwave sensor having a resonant strip transmission line for measuring the mass of a fibrous material. A half-wave of the electric field develops along the strip transmission line with intensity maxima at both ends, where there is a respective passage for a flow of product. The highly inhomogeneous fields at the open line ends are disadvantageous in terms of measurement techniques. Furthermore, it is necessary to shield the strip transmission line using a metallic enclosure in order to prevent falsification of the measurement through radiation loss. The enclosure has to be carefully adjusted in order to avoid resonance close to the measuring frequency. The construction of the sensor is therefore comparatively expensive.

It is an aim of the invention to provide an inexpensive microwave sensor having an improved measuring accuracy, and preferably to permit substantially exact measurement of a relatively large product quantity and/or an extensive product.

SUMMARY OF THE INVENTION

The invention provides a microwave sensor for measuring a dielectric property of a product comprising:

a microwave resonator chamber;

a microwave field generating device for generating a microwave field in the chamber; and a pathway for receiving the product in the chamber such that the product can interact with the microwave field;

wherein the chamber is such that it permits at least two half-waves of the electric field to be formed in the resonator and the pathway is arranged to transport the product through at least one region of high field intensity of said half-waves of the electric field.

The above aim can thus be achieved according to the invention in particular in that at least two half-waves of the electric field are formed in the resonator in one direction, the product feed being effected in at least one region of high field intensity of one of the half-waves of the electric field. By using at least two half-waves of the electric field, the invention enables the mass loading of the resonator in relation to the total energy stored in the resonator to be reduced, which enables the measuring accuracy to be improved and at high mass loading can possibly even prevent collapse of the electric field. According to the invention, the sample feed is arranged in a region of high field energy of at least one half-wave around a corresponding intensity maximum in order to achieve a high measuring sensitivity. This is a region having at least 50%, preferably at least 70%, more preferably at least 90% of the intensity in the field maximum. This delimits the invention from a higher-mode resonator such as that from EP 0 889 321 A, where the sample feed takes place into a central resonator region of very low field intensity.

Preferably, a product feed takes place into at least two resonator sections each corresponding to a respective half-wave of the electric field. This enables the product to be distributed over several half-waves of the electric field. This reduces the mass loading per half-wave and per resonator section. In particular, by increasing the number of half-waves the mass loading per resonator section can be reduced to a reasonable level. A relatively large expanse of a product in one direction can be covered by distribution onto several half-waves, wherein the extent of an individual region of high field strength can be relatively small. Instead of one large region of high field strength, several smaller regions of high field intensity are therefore provided, thereby enabling the overall size of the resonator as a whole to be reduced. The regions of high field strength are here generated inside a resonator; the use of several relatively small resonators is not necessary.

The term "half-waves of the electric field" describes in the case of a specific measuring frequency a concavity of the cos form field, that is, starting from a zero point of the field via a field maximum or minimum to the next zero point. A half-wave has an extent corresponding to a half wavelength. The use of at least two half wavelengths means that the cavity resonator is operated in a higher mode. In the case of a plurality of measuring frequencies, the term "half-wave" can refer to a field region that extends from a zero point of the field via a field maximum or minimum to the next zero point. Alternatively, the term can relate to the measuring frequency with the highest intensity.

Around the intensity maximum of a half-wave of the electric field there exists a region of approximately homogeneous intensity, which enables the measuring accuracy to be improved when the product is arranged in the intensity maximum. In many cases, the product is therefore arranged in at least two maxima of the electric field corresponding to the at least two half-waves. If a balanced mean value of the measuring quantity is to be obtained for all parts of the product, then the product portions are arranged in each resonator section advantageously substantially in the respective maximum of the electric field. By selectively varying the arrangement of individual product portions from the maximum in the respective resonator sections, any desired weighting of the individual product portions can be set.

The resonator can be of different constructions. Preferably, it is a shielded resonator or cavity resonator, that is, a cavity defined by metallic walls, which is substantially closed apart from openings for the sample feed. In the case of a cavity resonator, a cavity resonance is induced internally. This construction is especially inexpensive, compared, for example, to the strip transmission line of WO 00/55606 A. A rectangular resonator is especially simple and therefore preferred. The resonator can alternatively be a resonator opened especially via chokes. Nevertheless, the invention relates just to those resonators with which the product is introduced into or guided through the resonator chamber for measurement. The subject matter of the application is therefore delimited with respect to those (stray field) resonators in which measurement is effected by means of an external electric stray field, so that a completely different kind of field-strength distribution is present.

The invention is especially useful for measuring a continuous stream of product guided through the resonator, since here the product mass or product expanse is predetermined and cannot be matched to the resonator. This includes, in particular, strand-form and web-form products, for example, fibre products, tobacco, paper and the like. Also included is the measurement of individual production portions. In the case of a strand-form product, the at least two resonator sections are advantageously designed for passage of least one product strand each. It may be advantageous if two or even more product strands are guided through each resonator section, since if one fibre strand tears, it is carried along by the other strand. Preferably, however, not more than two product strands are guided through each resonator section, in order to keep the corresponding mass loading as low as possible.

The number and arrangement of the resonator sections can be freely matched to the particular requirements. The arrangement can be a one-dimensional, especially linear arrangement, for example, transversely across the width of a product web. An annular arrangement is also included, the at least two half-waves being arranged circumferentially. A two-dimensional arrangement is also possible, in which at least two half-waves of the electric field in the resonator are each provided in two directions. Even a three-dimensional arrangement is possible. The number of resonator sections amounts preferably to a least three, preferably at least four. Resonator sections that are not required can be allowed to run with no load. For example, a four-strand product can be measured with a resonator having four resonator sections, by guiding two strands through each of two resonator sections and running the two remaining resonator sections with no load. The same resonator construction (for example, a resonator with four resonator sections) can therefore be used for different applications (in the example mentioned, one to eight strands). Where appropriate, not all resonator sections have to have a product feed.

The resonator, if applicable the cavity resonator, can be filled with a solid dielectric having a dielectric constant greater than one, preferably at least two, more preferably at least five. Customary materials, especially ceramics, are known to the expert. The use of a dielectric filling enables field energy to be stored in a comparatively smaller space and therefore allows smaller forms of construction. Preferably, substantially the entire resonator is filled with dielectric, except for the space for receiving the sample. "Substantially" means apart from devices for coupling in microwaves, for guiding through the sample, and so on. The resonator can alternatively be filled substantially with air, however, which represents an especially simple and inexpensive construction.

The invention is essentially applicable both to a resonator operating on the basis of transmission measurement and to a resonator operating on the basis of reflection measurement.

The invention furthermore comprises an advantageous device for the inventive microwave sensor with a microwave resonator, especially for measuring the density of at least one sliver of textile fibres, for example of cotton, synthetic fibres or the like, in which the microwave sensor is used to control and/or to regulate a processing device for at least one textile fibre sliver.

The microwave sensor is advantageously arranged at the delivery end of a card. At least one microwave sensor is preferably arranged at the feed end and/or at the delivery end of the drawing system of a draw frame. The drawing system is advantageously a card drawing system at the delivery end of a card. The textile fibre sliver is preferably a card sliver. The textile fibre sliver is advantageously a draw frame sliver. The microwave sensor is preferably connected to an electronic control and regulating device, for example, a machine control and regulating device. The control and regulating device is advantageously connected to at least one actuator, for example, drive motor, for changing the density of the fibre sliver. An indicating device, for example, display screen, printer or the like, for displaying the density of or density changes in the fibre sliver is preferably connected to the control and regulating device. The microwave sensor is advantageously used to monitor the density of a sliver produced on a card or draw frame.

The invention further provides a microwave sensor for measuring a dielectric property, especially the density and/or moisture content of a product, having a microwave resonator wherein a product introduced into the resonator interacts with a resonant microwave field generated by a resonator in order to determine suitable measured quantities, especially for a spinning preparation machine, characterised in that at least two half-waves of the electric field are formed in the resonator in one direction, the product feed being effected in at least one region of high field intensity of one of the half-waves of the electric field.

BRIEF DESCRIPTION OF THE DRAWINGS

FIG. 5 is a plan view of a fourth embodiment of a sensor;
FIG. 6 is a view from the front of the sensor from FIG. 5;

DESCRIPTION OF PREFERRED EMBODIMENTS

Figure 1:
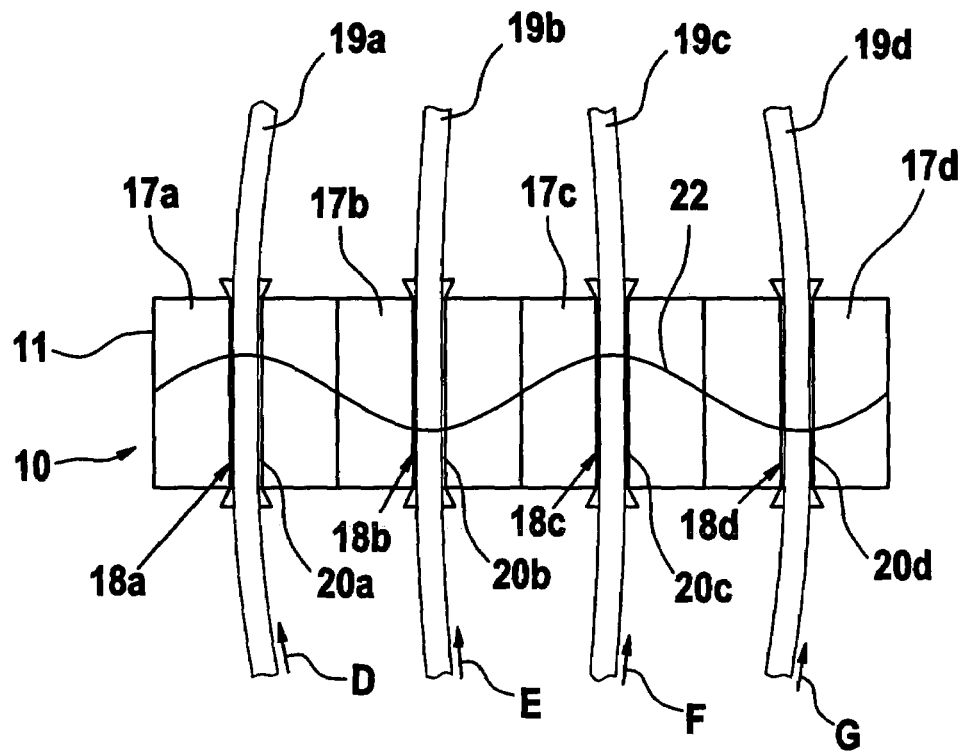
FIG. 1 is a plan view of a first embodiment of a sensor.
Figure 2:
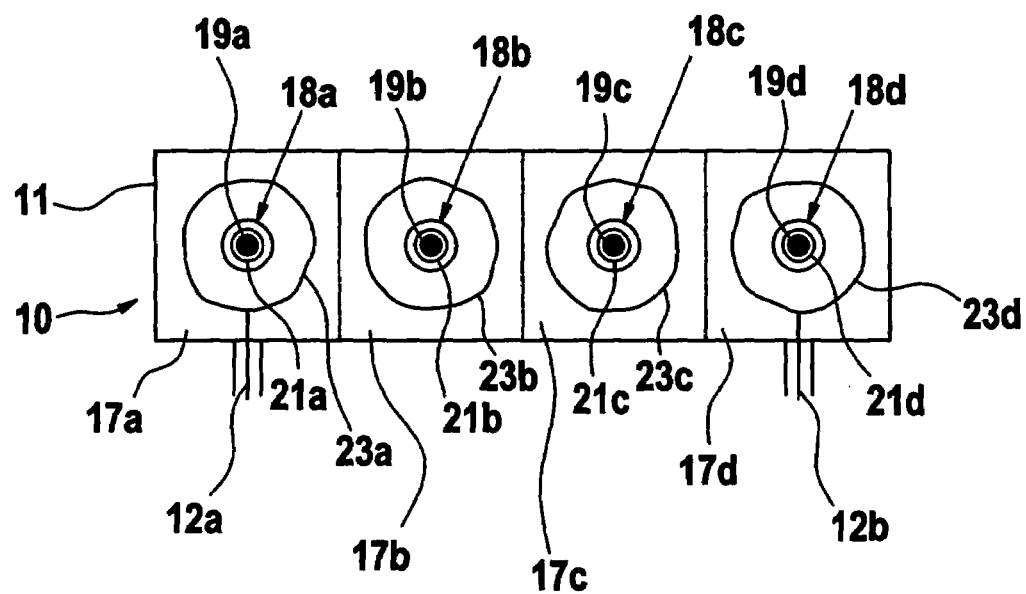
FIG. 2 is a view from the front of the sensor from FIG. 1.
Figure 8:
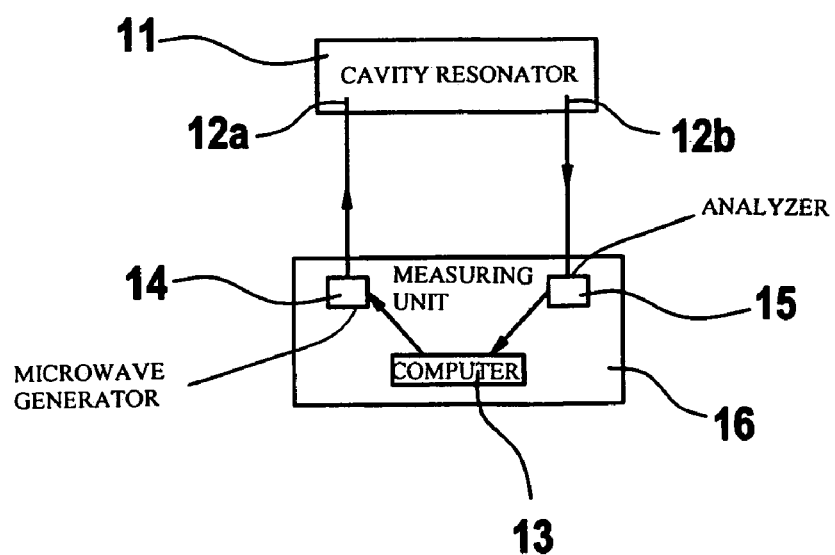
FIG. 8 is a diagrammatic sketch of a measuring arrangement having a sensor.

With reference to FIG. 1, a microwave sensor 10 comprises a cavity resonator 11, in which a standing microwave field is generated. The coupling and decoupling of the microwave field is effected by means of coupling devices 12. Microwaves are generated by means of a generator 14 controlled by a computer 13 and are relayed by means of a line to the coupling device 12a. A microwave signal is decoupled from the resonator 11 via the coupling device 12b and fed by means of a line to an analyser 15, the output signal of which can be processed by the computer 13. Generator 14, analyser 15 and computer 13 are expediently combined in one measuring unit 16 (cf. FIG. 8). The arrows D, E, F and G indicate the direction of flow of the material.

Figure 3:
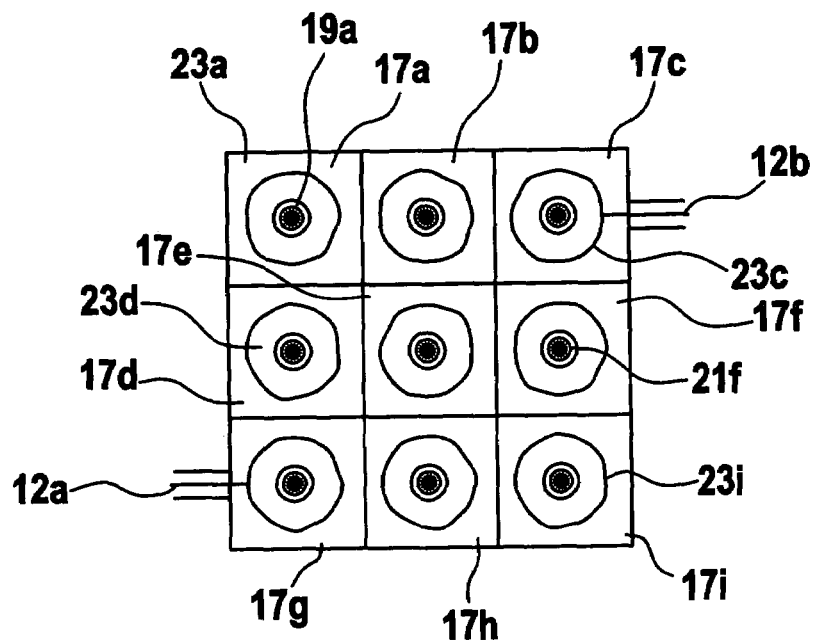
FIG. 3 is a view from the front of a second embodiment of a sensor.
Figure 4:
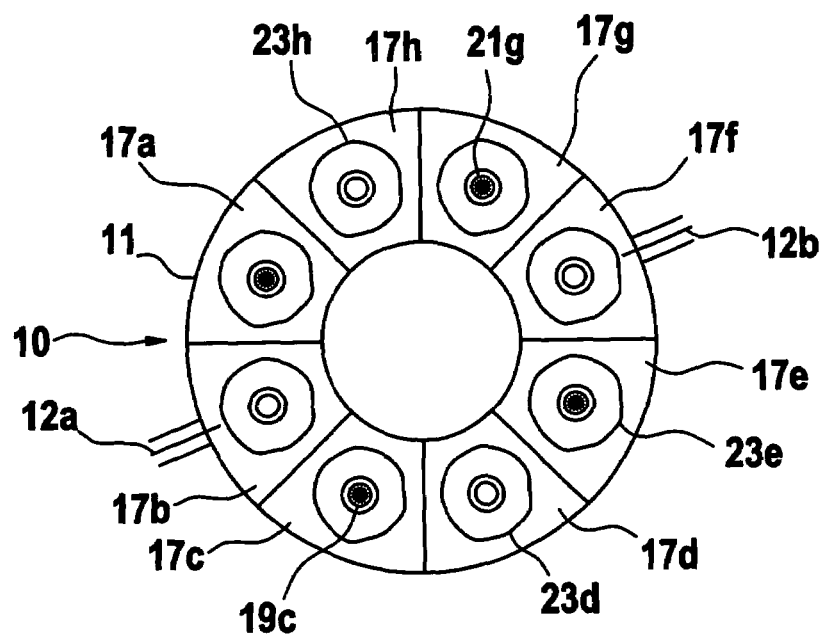
FIG. 4 is a view from the front of a third embodiment of a sensor.

The resonator 11 has a plurality of resonator sections 17a, 17b, 17c, . . . . The division into different resonator sections is indicated in the Figures by broken lines. FIGS. 1, 2, 5, 6, 7 and 9 each relate to elongate rectangular cavity resonators having, for example, four or two resonator sections. Elongate means that the extent along a longitudinal axis is longer by at least a factor of two, preferably by at least a factor of three, more preferably by a factor of at least five than the extent along the two directions perpendicular to the longitudinal axis. The resonator sections 17 are arranged in series along the longitudinal axis of the resonator 11. FIG. 3 shows a resonator in which the resonator sections are arranged in columns and rows, that is, in the form of a matrix. The number of columns, rows and generally the arrangement of the resonator sections can be adapted as desired to the particular requirements. FIG. 4 relates to an annular resonator 11, in which the resonator sections 17 are arranged in series along the annular axis of the resonator 11. In this example, four resonator sections 17b, 17d, 17f, 17h run with no load. Generally, any desired number of resonator sections 17 can run with no load.

For sample feed, each resonator section has openings 21a, 21b, 21c, . . . , which can be provided in particular in walls defining the resonator. In the case of measurements on a product flow, especially on a strand-form product flow (FIGS. 1 to 4 and 7) or a web-form product flow (FIGS. 5, 6), advantageously respective separate openings 21 are provided for entry and exit of the sample 19 into respectively from the resonator 11. Preferably, the size of the openings 21 corresponds approximately to the cross-section of the product 19 to be measured. Preferably, the form of the openings 21 is matched to the cross-section of the product. For example, in the case of a strand-form product, the openings 21 are therefore preferably circular or oval. The resonator is preferably substantially closed except for the product feed openings 21. "Closed" means impermeable to the microwaves used. The above-mentioned features contribute to the reduction in unfavourable radiation of microwave energy from the resonator.

To pass the product 19 through the resonator 11 or resonator sections 17, sample guide devices 18a, 18b, 18c, . . . can be provided, for example, small tubes 20a, 20b, 20c, . . . , which can preferably consist of low-loss dielectric having a low temperature dependence, for example, quartz glass.

Figure 9:
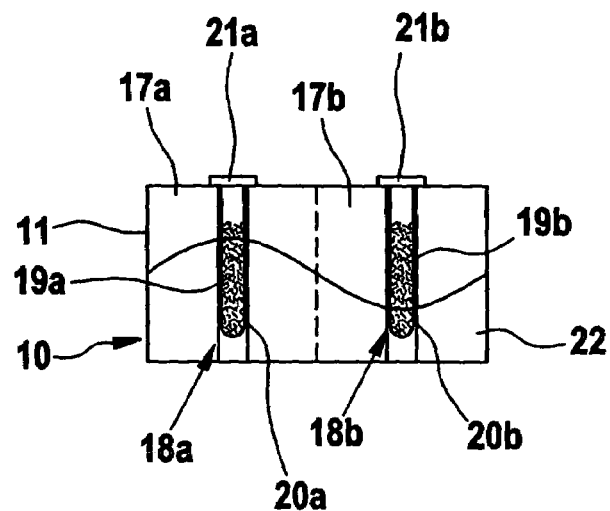
FIG. 9 is a plan view of a sixth embodiment of a sensor.

The internal dimensions of the resonator chamber and the frequency of the microwaves are such that a standing wave having a plurality of half-waves can develop in the resonator. In practice, the microwave frequency generated by the generator 14 is adapted so that a standing wave having at least two convex half-waves, each with a local intensity maximum, develops in the resonator 11. In FIGS. 1, 5 and 9, electric field lines 22 for the case of a microwave of specific frequency are drawn in by way of example. In this case, a cos form half-wave of the electric field propagates per resonator section 17. Any other field distributions having at least two half-waves, also of more than one frequency, in general of any frequency distribution, and/or several maxima per resonator section, are likewise possible. In FIGS. 2 to 4, 6 and 7, lines 23 of constant field intensity are drawn in. Inside the lines 23 there lies a region of high field intensity with a local intensity maximum, which lies approximately at the centre of the respective resonator section. Generally, this is not absolutely necessary. The field intensity is less outside the lines 23 than inside.

By distributing the entire production flow 19 over a plurality of resonator sections 17, the mass loading per resonator section 17 is correspondingly reduced, in the example of FIG. 1, by a factor of four for example, in the example of FIG. 3 by a factor of nine for example. The individual portions of the sample 19 are each guided through a region of the respective resonator section 17 arranged closely around the respective intensity maximum. As is apparent in FIG. 1, for example, in this region the field strength is approximately constant. Positional and orientation changes of the sample as well as spatial inhomogeneities within the product flow have therefore no or at most slight effect on the measuring signal, since all portions of the product flow enter the measuring signal with the same weighting—owing to the approximately constant field strength—as evident in the examples of FIGS. 1 to 4, 7 and 9. One opening 21 can be specifically arranged away from the respective intensity maximum in order to permit individual weightings of individual production portions.

The embodiment according to FIGS. 5 and 6 relates to the measurement of a sheet-form product 31, especially a panel-form or web-form product, for example, paper, fibre fleece or the like. The opening 21 is slot-form, the slot 30 comprising slot sections 21a, 21b, 21c, 21d. The length of the slot 30 is matched to the width of the paper web 31.

To measure a paper web 31 of twice as long, this same measuring unit 16 can be used at the same microwave frequency, by simply selecting a linear arrangement of eight instead of four resonator sections 17, whereby the length of the resonator 11 would be approximately doubled.

In this way, the overall size of the resonator 11 needs to be changed only along the longitudinal axis, that is, in only one dimension, whilst the overall size of the resonator 11 can remain otherwise unchanged. The reference numeral H denotes the direction of flow of the material.

Generally, it is not necessary for the slot 30, as in the example of FIGS. 5 and 6, to be closed. The resonator 11 can consist of two separate resonator halves, forming between them a sample feed slot. Preferably, the microwave coupling devices 12 are each arranged in different resonator halves. It is also possible to measure strand-form products using a slotted resonator.

Figure 7:
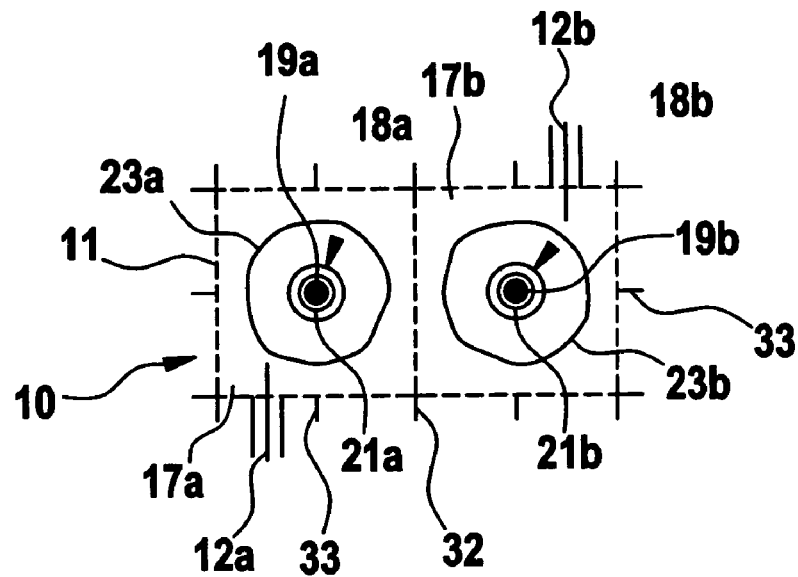
FIG. 7 is a plan view of a fifth embodiment of a sensor.

The embodiment shown in FIG. 7 illustrates that the walls of the resonator 11 are not completely closed, but are merely intended to be substantially impermeable to microwaves. In the case of FIG. 7, separating devices 32, 33, for example, separating plates, are provided, which are arranged preferably at intervals from one another at a spacing that is less than the wavelength of the microwave field corresponding to the propagation limit frequency. The field can spill out a little between the separating plates 32, but as a whole is concentrated substantially in the interior of the resonator 11.

The embodiment shown in FIG. 9 relates to a resonator 11 for measuring portions of a product 19. The individual portions can be disposed in a sample container 33, for example, a quartz glass tube. The resonator 11 has per resonator section 17a, 17b just one opening 21 in the resonator walls for introduction of the product 19. This can be effected automatically, for example, by means of a robot. Guide means 20 are preferred but are not obligatory. Also in this example, at a relatively low mass loading per resonator section 17 a relatively large sample mass can be measured with just one resonator 11.

Figure 10:
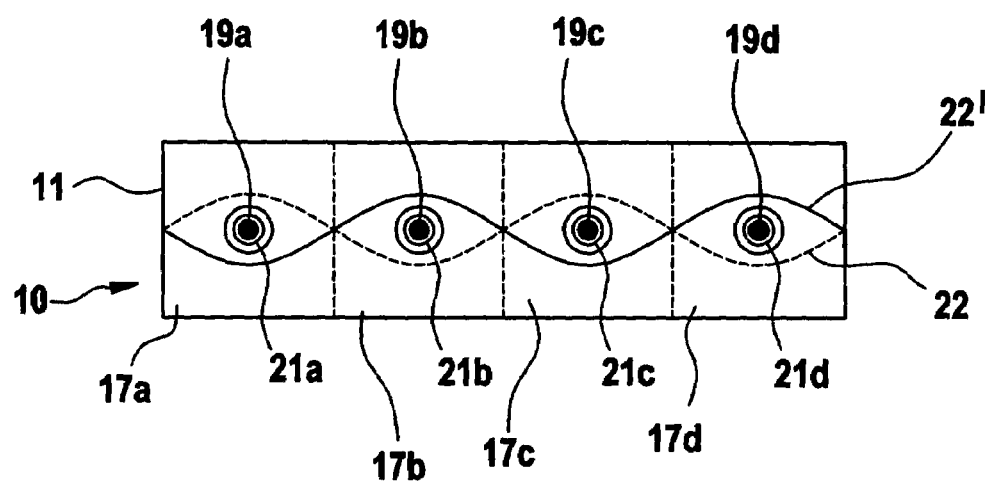
FIG. 10 shows the sensor from FIG. 5, the product in each resonator section being arranged substantially in the respective maximum of the electronic field.

Referring to FIG. 10, the fibre slivers 19a, 19b, 19c and 19d are arranged in each resonator section 17a, 17b, 17c and 17d respectively substantially in the respective maximum of the electric field. A half-wave of the electric field propagates per resonator section 17a to 17d.

Figure 11:
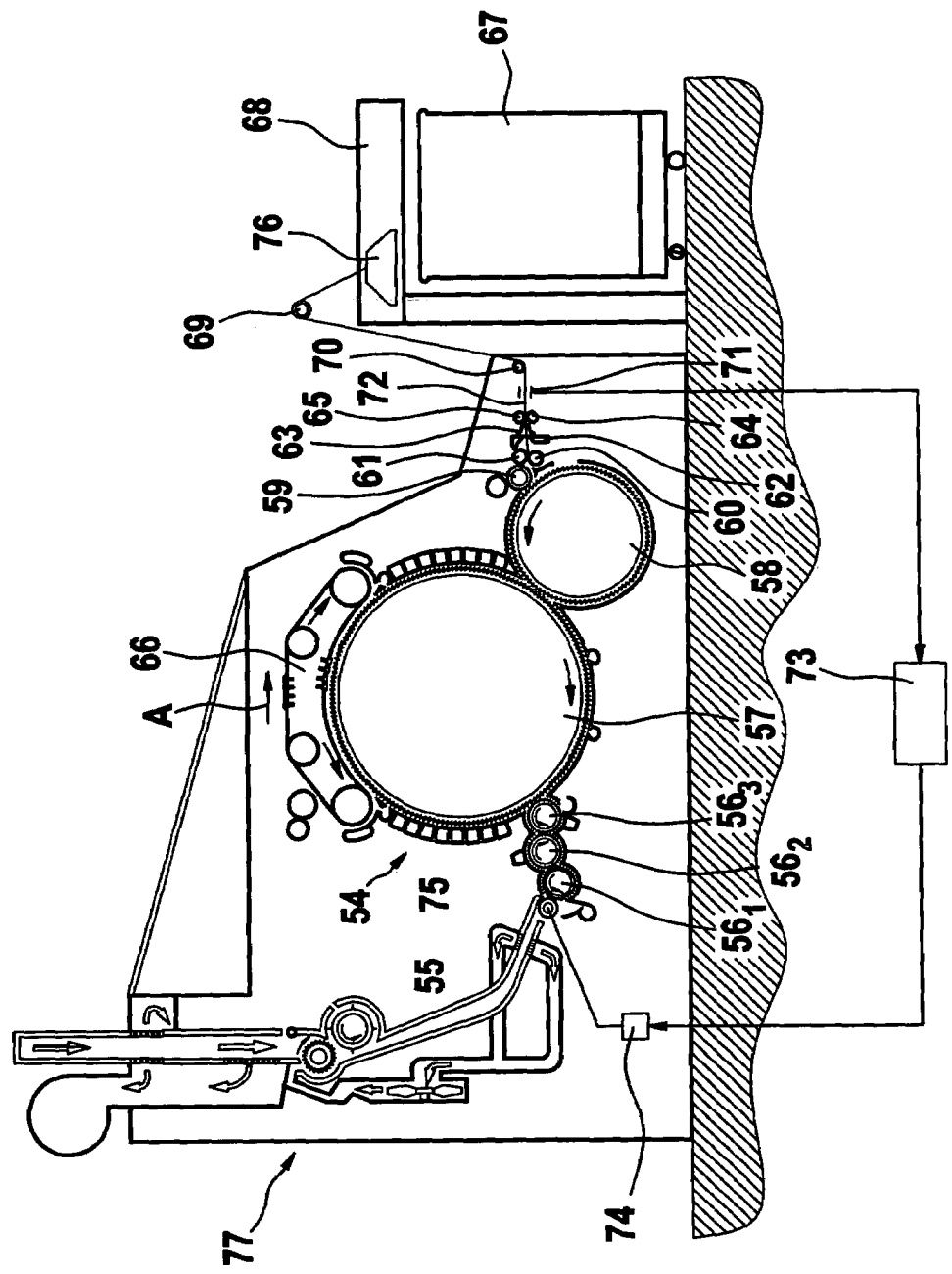
FIG. 11 shows schematically in side view a card with the microwave sensor according to the invention.

FIG. 11 shows a carding machine 54, for example, a carding machine known as a TC 03 made by Trutzschler GmbH & Co. KG of Mönchengladbach, Germany, with feed roller 55, feed table 75, licker-ins 56$_1$, 56$_2$, 56$_3$, cylinder 57, doffer 58, stripping roller 59, squeezing rollers 60, 61, web-guide element 62, web funnel 63, take-off rollers 64, 65, revolving card top 66, can coiler 68 and can 67. The directions of rotation of the rollers are shown by respective curved arrows. The take-off rollers 64, 65 draw off a card sliver 72, which passes over guide rollers 69, 70 to the can coiler 68 and from there is laid in the can 67. The microwave measuring arrangement 71 according to the invention (see FIG. 1, 2) is arranged between the take-off rollers 64, 65 and the guide roller 69. The microwave measuring arrangement 31 is connected to an electronic control and regulating device 73, for example, a microcomputer, which alters the rotational speed of the feed roller 55 by way of a variable speed drive motor 74. In this way, the density of the card sliver 72, which can leave the take-off rollers 64, 65 at high speed, for example, 200 m/min or more, is adjusted. The letter A denotes the direction of working. The reference numeral 77 denotes a tuft feed device, for example, a DIRECTFEED tuft feed device made by Trützschler GmbH & Co. KG, which provides a fibre tuft fleece to the feeding device of the card 54.

Figure 12:
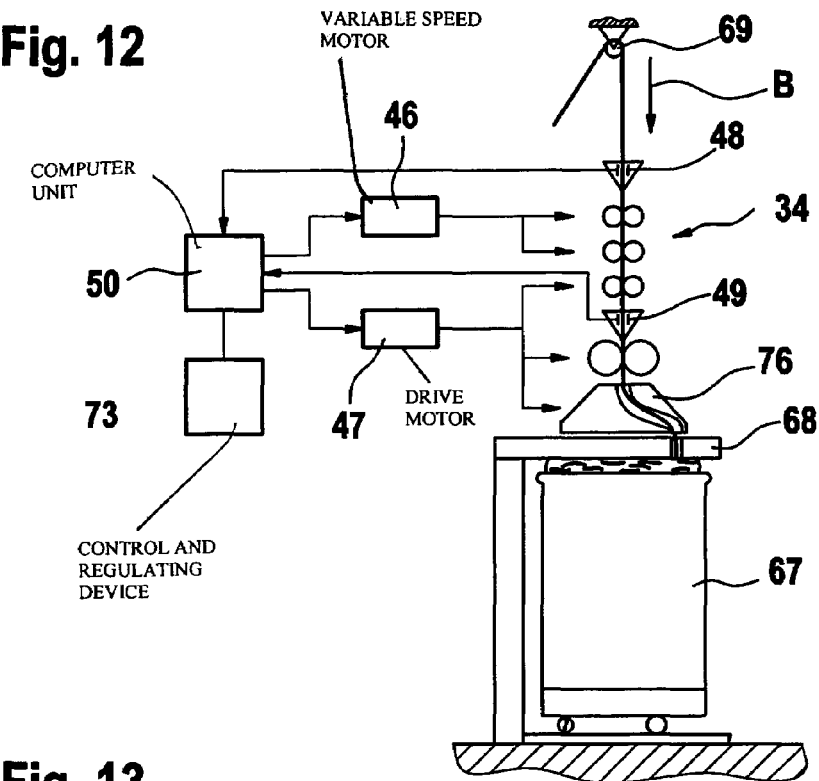
FIG. 12 shows a can coiler with fibre sliver can with an autoleveller drawing system with the microwave sensor according to the invention.
Figure 13:
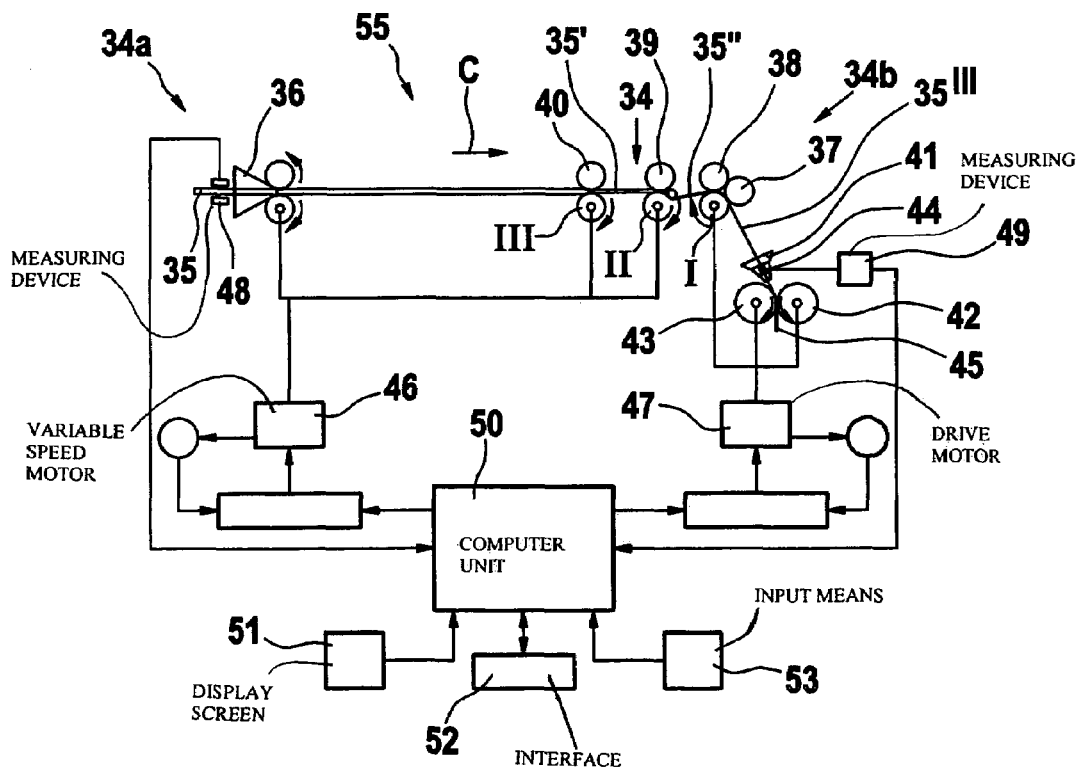
FIG. 13 is a diagrammatic side view of an autoleveller draw frame having a respective microwave sensor according to the invention.

Referring to FIG. 12, a drawing system 34, which corresponds to the drawing system shown in FIG. 13, is arranged above the can coiler 68; reference will be made to the description of the drawing system of FIG. 13. At the feed end and delivery end of the drawing system 34 there is a respective microwave measuring arrangement 48, 49, which are connected to the central computer unit 50 (e.g., electronic control and regulating device), which is furthermore connected to a drive motor 46 for the feed and middle pairs of rollers and a drive motor 47 of the delivery roller pair, take-off rollers and the can turntable 76.

Referring to FIG. 13, a draw frame 55, for example, a draw frame TD 03 made by Trützschler GmbH & Co. KG, has a drawing system 34, upstream of which is a drawing system feed 34a and downstream of which is a drawing system outlet 34b. The fibre slivers 35 enter the sliver guide 36 from cans (not shown) and, drawn by the take-off rollers, are transported to the drawing system 34. The drawing system 34 is designed as a 4-over-3 drawing system, that is, it consists of three bottom rollers I, II, III (I being the bottom delivery roller, II being the bottom middle roller and III being the bottom feed roller) and four top rollers 33, 38, 39, 40. Drafting of the composite fibre sliver 35'', comprising several fibre slivers 35, takes place in the drawing system 34. The draft is made up from the preliminary draft and the main draft. The roller pairs 40/III and 39/II form the preliminary drafting zone and the roller pairs 39/II and 38, 37/I form the main drafting zone. The drawn fibre slivers 35''' reach a web guide 41 at the outlet 34b of the drawing system and are drawn by means of the take-off rollers 42, 43 through a sliver funnel 44 in which they are condensed to a fibre sliver 45, which is subsequently deposited in a can (not shown). The letter C denotes the working direction, and 35'' denotes the fibre slivers in the drawing system. The take-off rollers, the bottom feed roller III and the middle bottom roller II, which are mechanically linked, for example, by way of toothed belts, are driven by the variable speed motor 46, it being possible to pre-set a desired value. (The associated top rollers 39 and 40 co-rotate). The bottom output roller I and the take-off rollers 42, 43 are driven by the main motor 47. At the inlet 34a to the drawing system, a variable proportional to the density of the fed-in fibre slivers 35 is measured by the microwave sensor 48 (intake-side measuring device) according to the invention. At the outlet 34b of the drawing system 34, the density of the fibre sliver is obtained by a microwave sensor 49 (delivery-side measuring device) according to the invention associated with the sliver funnel 44. A central computer unit 50 (control and regulating device), e.g. a microcomputer with microprocessor, determines a setting of the regulated variable for the variable speed motor 46. The measured variables of the two measuring devices 48 and 49 are sent during the drawing process to the central computer unit 50. From the measured variables of the feed-side measuring device 48 and from the desired value for the density of the emerging fibre sliver 45, the adjustment value for the variable speed motor 46 is determined in the central computer unit 50. The measured variables of the delivery-side measuring device 49 are used to monitor the emerging fibre sliver 45 (monitoring of delivered sliver).

By means of this control system, fluctuations in the density of the fed-in fibre slivers 35 can be compensated by corresponding adjustments to the drafting process and the fibre slivers can be evened out. The reference numeral 51 denotes a display screen, 52 denotes an interface and 53 denotes an input means.

Figure 14:
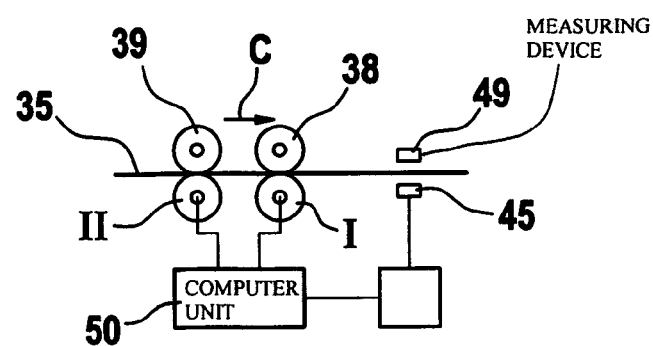
FIG. 14 shows an autoleveller draw frame with a closed control loop (regulation) and the measuring arrangement according to the invention.
Figure 15:
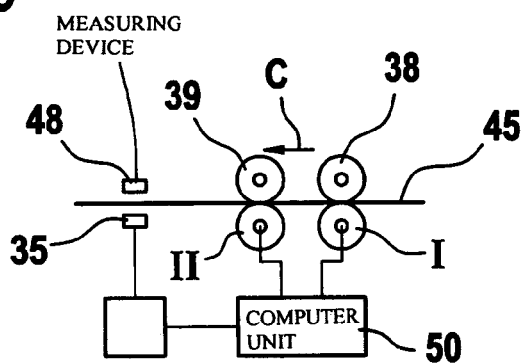
FIG. 15 shows an autoleveller draw frame with an open control loop (control), and the measuring arrangement according to the invention.
Figure 16:
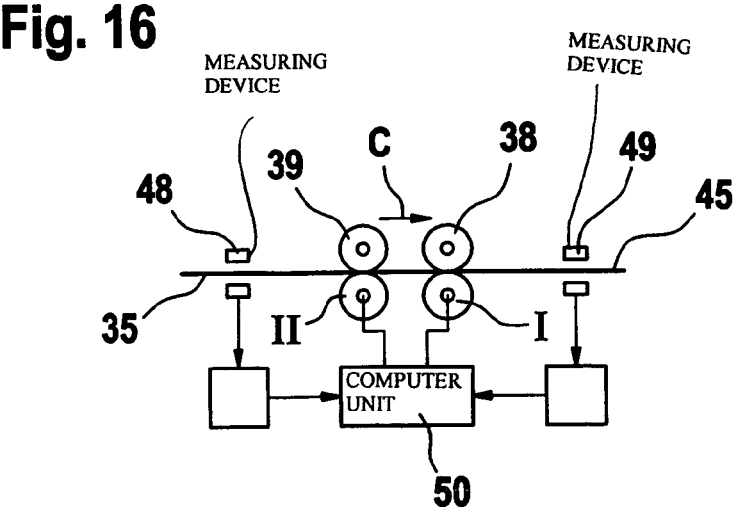
FIG. 16 shows an autoleveller draw frame with a combination of an open and a closed control loop (reference variable input) and two measuring arrangements according to the invention.

FIGS. 14, 15 and 16 show basic layouts of the drawing system of a draw frame with different constructions for the adjustment of the fibre sliver density. FIG. 14 shows a closed control loop, in which the microwave measuring arrangement 49 is arranged at the delivery end of the drawing system. The fibre material leaving the drawing system passes through the measuring arrangement 49, the output signal of which is compared in the central computer unit 50 with a desired value and is converted so that a corresponding control signal is supplied to an actuator (variable speed motor 46, see FIG. 13) for the roller II. The output signal corresponding to the density of the emerging fibre material thus influences the speed ratio of the drafting roller pairs 39/II and 38/I in the sense that the fibre material is evened out. FIG. 15 shows an open control loop (control). Here, the microwave measuring arrangement 48 is located in the region in which the fibre material 35 approaches the drawing system, measures the density of the fibre material and the corresponding measuring signal is converted in the central computer unit 50 into a control signal which is supplied to an actuator (variable speed motor 46, see FIG. 13) for the roller II. Allowances are made electronically for the time taken by the fibre material 35 to run from the measuring arrangement 48 to the drawing system. FIG. 16 shows a combination of an open and a closed control loop, in which the measuring signals of the measuring arrangement 49 are superimposed on the measuring signals of the measuring arrangement 48.

"Resonator" relates to a spatial region in which a standing microwave field is able to propagate. The resonator can be a closed or a substantially closed cavity resonator.

A product of which the density is being measured is arranged in an area called a "product area", which, when the sensor is operative, is in a fixed spatial relationship with the area of the resonator. The microwaves enter the product area in order to interact with the product. The microwave resonator is permeable to microwaves towards the product area. The product can be a consecutive and/or continuous stream of product, for example, a fibre sliver, a fibre web, fibre tufts or individual fibres in spinning preparation machines.

Figure 17:
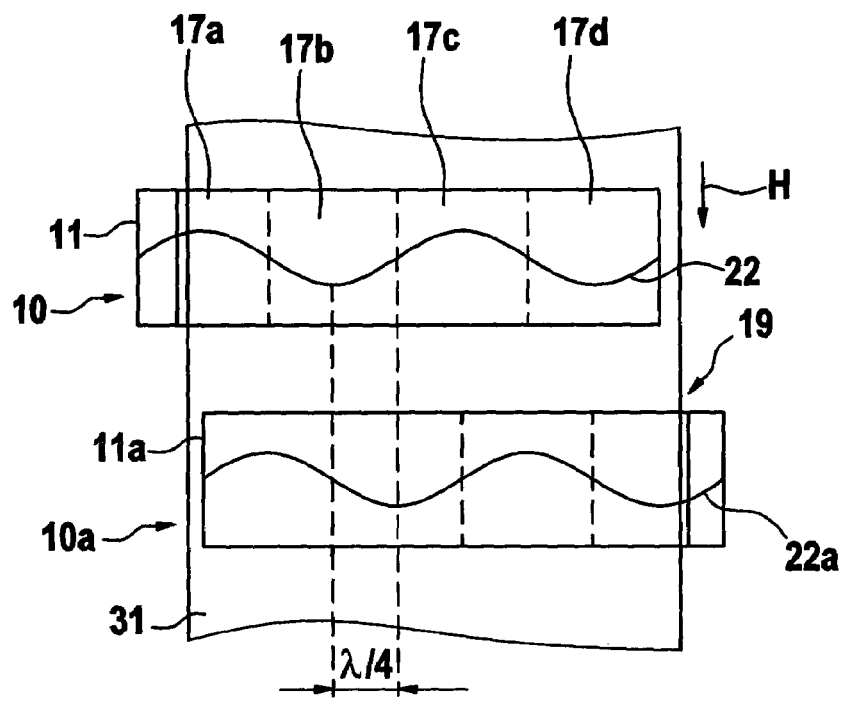
FIG. 17 shows as further embodiment of the invention in which a second, downstream, sensor is arranged in an offset position relative to a first, upstream, sensor.
Figure 18:
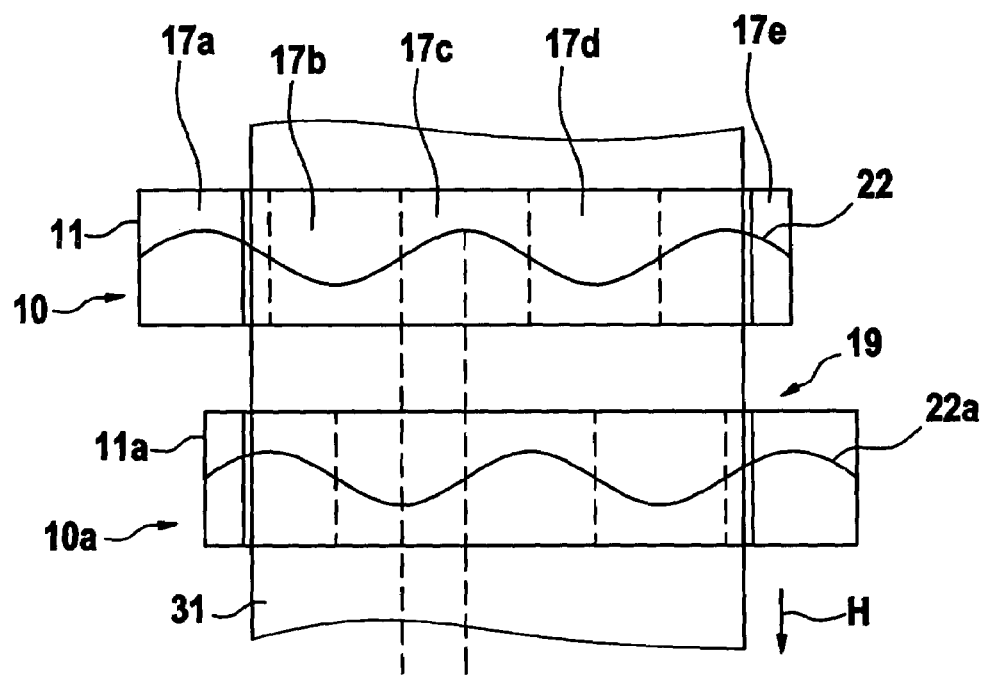
FIG. 18 shows an embodiment similar to that of FIG. 17, in which the second sensor is offset in the opposite direction.

FIGS. 17 and 18 show two further embodiments of the invention, in which two microwave sensors 10, 10*a* are arranged perpendicular to the direction of flow H of the material offset by a quarter of a wavelength $\lambda/4$ with respect to one another. The sensors 10, 10*a* with a respective resonator 11, 11*a* are electrically coupled (not shown) with one another. The signals of the sensors 10, 10*a* are electrically totalled and evaluated (not shown). In this way, in the case of a flat product, for example, textile fibre fleece, the maxima of the electric fields 22 and 22*a* are better exploited.

Although the foregoing invention has been described in detail by way of illustration and example for purposes of understanding, it will be obvious that changes and modifications may be practised within the scope of the appended claims.

What is claimed is:

1. A microwave sensor for measuring a dielectric property of a product comprising:
    a microwave resonator chamber;
    a microwave field generating device for generating a microwave field in the resonator chamber; and
    a pathway adapted to guide the product through the resonator chamber such that the product is exposed to the microwave field;
    wherein the resonator chamber is adapted for at least two half-waves of the electric field to be formed in the resonator chamber, and the pathway is arranged to guide the product through at least one region of high field intensity of said half-waves of the electric field.

2. A microwave sensor according to claim 1, in which the resonator chamber has at least two resonator sections, each having a dimension corresponding to a respective half-wave of the electric field.

3. A microwave sensor according to claim 2, in which the resonator chamber has a dimension corresponding to at least three half-wave lengths of the electric field.

4. A microwave sensor according to claim 1, in which the resonator chamber is a cavity resonator.

5. A microwave sensor according to claim 1, in which the pathway is arranged to guide a product flow through the resonator chamber.

6. A microwave sensor according to claim 1, in which the resonator chamber has resonator openings for the sample feed that correspond substantially to the cross-section of the product to be fed in.

7. A microwave sensor according to claim 1, in which the pathway is arranged to guide the product feed through a region of high field intensity of the half-waves of the electric field.

8. A microwave sensor according to claim 7, in which the pathway is arranged to guide the product feed through the intensity maximum of the half-waves of the electric field.

9. A microwave sensor according to claim 7, in which the position of the product feed is adjustable relative to an intensity maximum of the electric field.

10. A microwave sensor according to claim 1, in which a multiplicity of resonator sections each corresponding to a respective half-wave of the electric field are linearly arranged.

11. A microwave sensor according to claim 1, in which the resonator chamber is filled with a dielectric.

12. A microwave sensor according to claim 1, in which a separate pathway for a respective product feed is provided with each half-wave of the electric field.

13. A microwave sensor according to claim 1, in which each resonator section corresponding to a half-wave of the electric field has a pathway which provides for feed of at least two product strands or webs.

14. A microwave sensor according to claim 1, in which the resonator chamber has a slot extending over a plurality of half-waves for sample feed-through.

15. A microwave sensor according to claim 14, in which the resonator chamber is suitable for measurement of a sheet-form product.

16. A microwave sensor according to claim 15, in which the resonator chamber has a dimension corresponding to a number of half-waves of the electric field that is matched to the width of the sheet-form product.

17. A microwave sensor according to claim 1, which is suitable for monitoring textile fibre material.

18. The microwave sensor according to claim 17, in which the textile fibre material is at least one of a fibre sliver or a non-woven web of textile material.

19. A sensor according to claim 1, which is connected to a control and regulating device of a textile machine.

20. A sensor according to claim 19, in which at least one actuator, for changing the density of the fibre material is connected to the control and regulating device.

21. A sensor according to claim 20, in which the actuator is a variable speed drive motor.

22. A sensor according to claim 19, comprising an indicating device for displaying the density of the fibre material, the indicating device being connected to the control and regulating device.

23. A control device comprising a microwave sensor according to claim 1, in which data from the microwave sensor is used to control a processing device for at least one of a textile fibre sliver or a non-woven web of textile material.

24. A device according to claim 23, in which the microwave sensor is used to monitor the density of the sliver produced on a carding machine or draw frame machine.

25. A device according to claim 23, in which the microwave sensor is arranged at the delivery end of a carding machine.

26. A device according to claim 23, in which at least one microwave sensor is arranged at at least one of the feed end or the delivery end of a drawing system.

27. A device according to claim 26, in which the drawing system is a drawing system of a draw frame machine.

28. A control device comprising a microwave sensor according to claim 1, in which data from the microwave sensor is used to control a processing device for a textile fibre fleece.

29. A device according to claim 28, which is arranged to measure a textile fibre fleece at the delivery end of a card.

30. A device according to claim 28, which is arranged to measure a textile fibre tuft fleece at the feed end of a card.

31. A device according to claim 28, in which two microwave sensors are arranged perpendicular to the direction of flow of the material, offset by a quarter of a wavelength with respect to one another.

32. A device according to claim 31, in which the sensors are coupled to one another and the signals of the sensors are added and evaluated.

33. A microwave sensor for measuring a dielectric property of a product in a spinning preparation machine, the microwave sensor comprising a microwave resonator chamber having a pathway extending therethrough, and a resonator adapted to form a resonant microwave field, wherein a product introduced into the pathway interacts with the resonant microwave field in order to determine suitable measured quantities, further wherein at least two half-waves of the microwave field are formed in the resonator in one direction, and the pathway guides the product through at least one region of high field intensity of one of the half-waves of the electric field.

34. The microwave sensor of claim 33, wherein the dialectric property of the product is at least one of density or moisture content.

* * * * *